(12) United States Patent
Taylor et al.

(10) Patent No.: US 7,033,358 B2
(45) Date of Patent: Apr. 25, 2006

(54) VERTEBRAL ARTHRODESIS EQUIPMENT

(76) Inventors: Jean Taylor, 25, avenue Poralto, F-06400 Cannes (FR); Bernard Villaret, 20, rue de Salles, F-17220 Croix Chapeau (FR); Patrizio Parisini, Via Pastrengo no 8, I-40123 Bologna (IT); Jean-Luc Clement, 230, chemin Monfort, F-06480 La Colle sur Loup (FR); Yves Adam, 4 Route de Saint Louet, F-14280 Authie (FR)

( * ) Notice: Subject to any disclaimer, the term of this patent is extended or adjusted under 35 U.S.C. 154(b) by 0 days.

(21) Appl. No.: 10/416,031

(22) PCT Filed: Nov. 5, 2001

(86) PCT No.: PCT/FR01/03411

§ 371 (c)(1), (2), (4) Date: Oct. 20, 2003

(87) PCT Pub. No.: WO02/38060

PCT Pub. Date: May 16, 2002

(65) Prior Publication Data

US 2004/0064140 A1    Apr. 1, 2004

(30) Foreign Application Priority Data

Nov. 7, 2000    (FR) .................................. 00 14274

(51) Int. Cl.
*A61B 17/70*    (2006.01)
(52) U.S. Cl. .................................................... 606/61
(58) Field of Classification Search .................. 606/60, 606/61, 72, 73; 623/17.11
See application file for complete search history.

(56) References Cited

U.S. PATENT DOCUMENTS

| | | | | |
|---|---|---|---|---|
| 4,269,178 | A | * 5/1981 | Keene | 606/61 |
| 5,346,493 | A | * 9/1994 | Stahurski et al. | 606/61 |
| 5,380,325 | A | * 1/1995 | Lahille et al. | 606/61 |
| 5,628,740 | A | * 5/1997 | Mullane | 606/61 |
| 5,653,710 | A | * 8/1997 | Harle | 606/73 |
| 5,702,392 | A | * 12/1997 | Wu et al. | 606/61 |
| 5,725,528 | A | * 3/1998 | Errico et al. | 606/61 |
| 5,938,663 | A | * 8/1999 | Petreto | 606/61 |
| 6,066,140 | A | * 5/2000 | Gertzbein et al. | 606/61 |
| 6,299,614 | B1 | * 10/2001 | Kretschmer et al. | 606/61 |
| 6,352,537 | B1 | * 3/2002 | Strnad | 606/61 |

FOREIGN PATENT DOCUMENTS

NL    1 011 260 C    8/2000
WO    WO 98/55038    12/1998

* cited by examiner

*Primary Examiner*—Eduardo C. Robert
*Assistant Examiner*—David Cornstock
(74) *Attorney, Agent, or Firm*—Young & Thompson

(57) ABSTRACT

An equipment includes at least a shoring rod and at least an anchoring assembly of the shoring rod to a vertebra; each anchoring assembly comprises a base integral with a hook which has substantially planar part, extending in a parallel plane, or forming a slight angle, less than 15 degrees, with the base. The base has a hole which runs right through it, having an oblong cross-section, and the anchoring assembly comprises a hook-shaped component whereof the part corresponding to the base of the hook is linked to a threaded rod capable of being engaged in the hole with the possibly of pivoting about an axis and of displacement in the plane, and capable of receiving a screw.

5 Claims, 3 Drawing Sheets

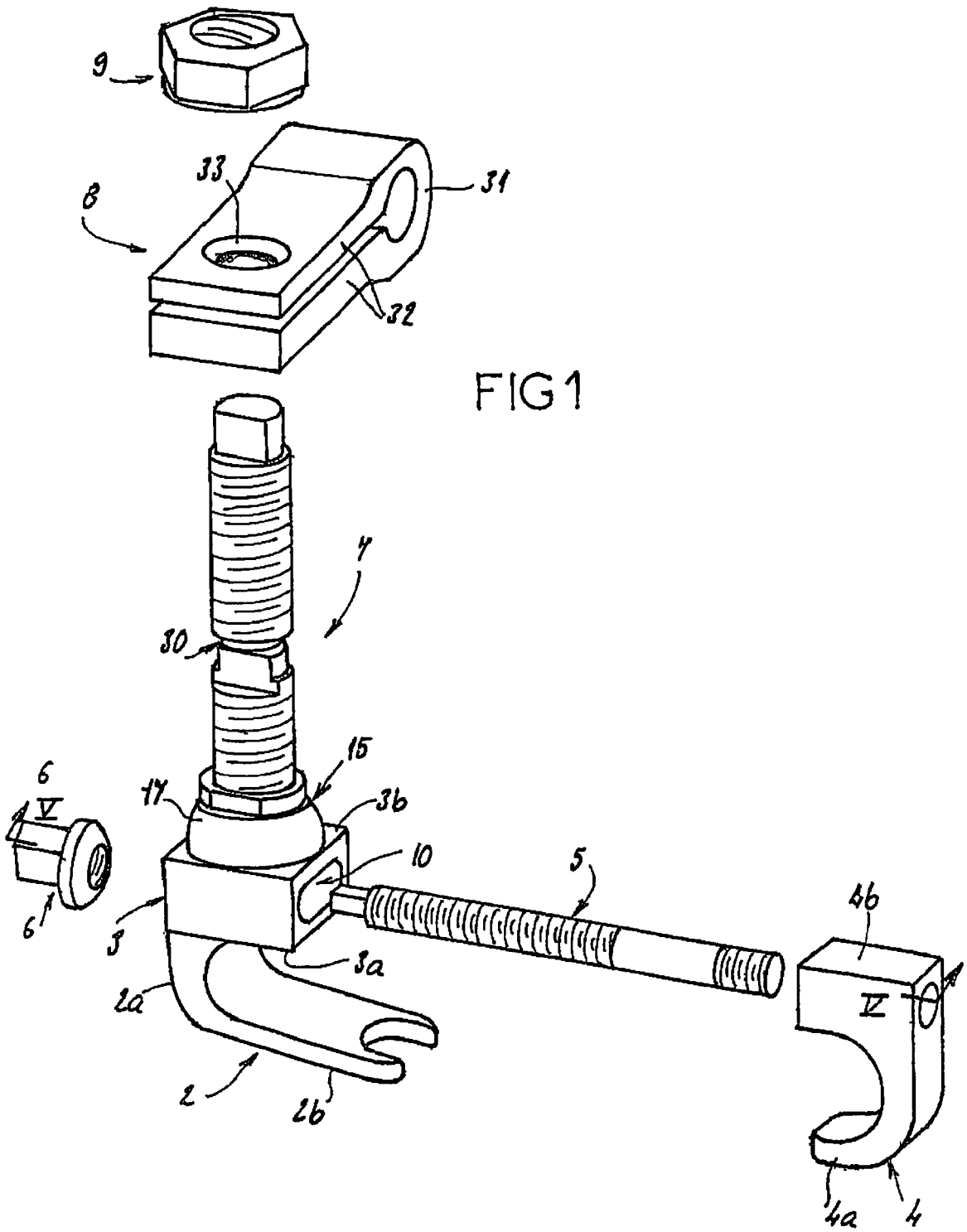

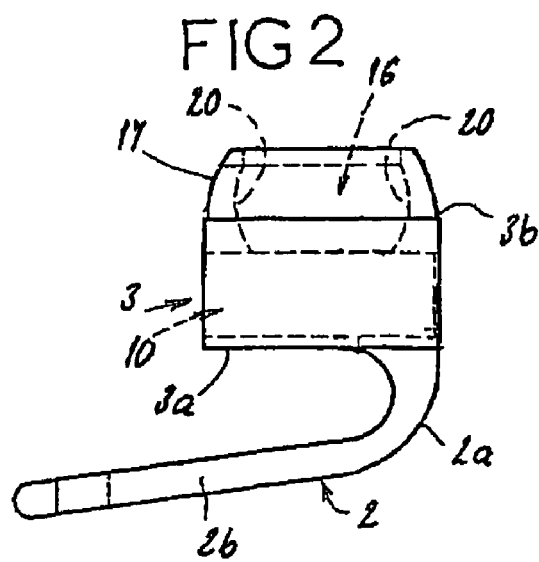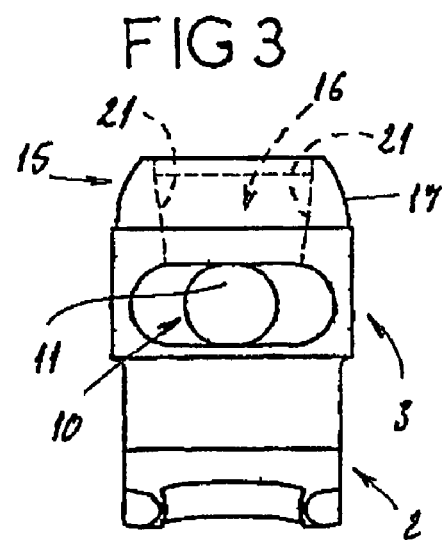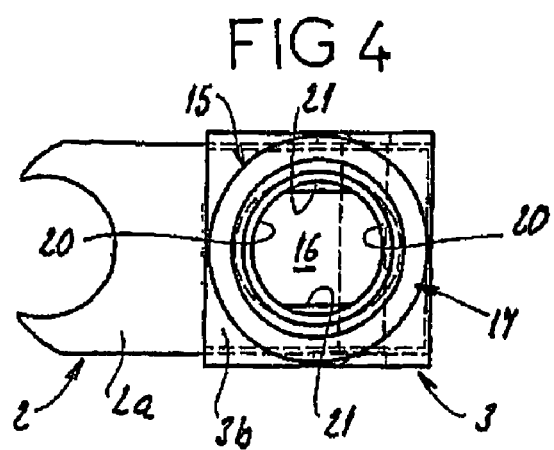

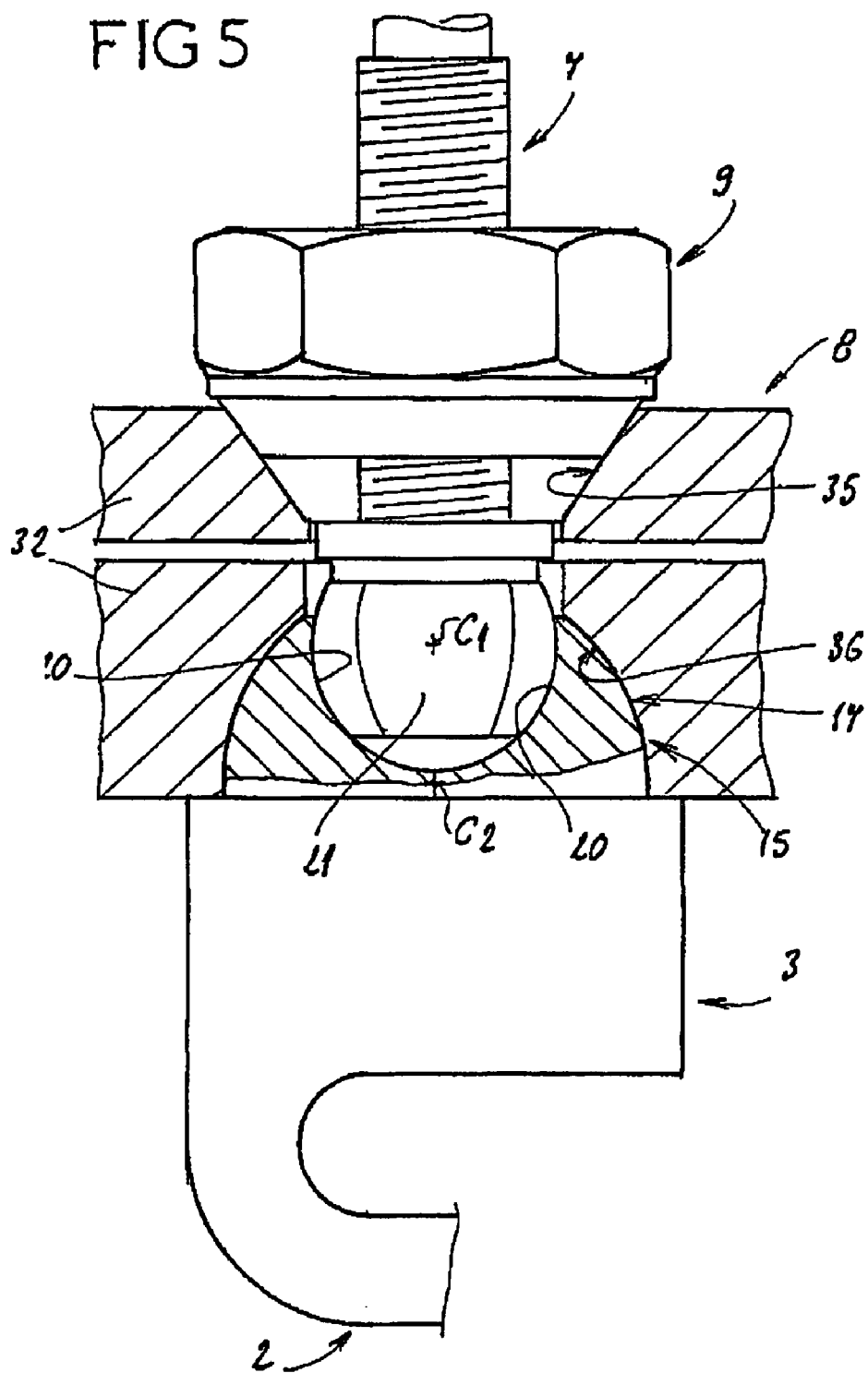

VERTEBRAL ARTHRODESIS EQUIPMENT

CROSS REFERENCE TO RELATED APPLICATION

This is the 35 USC 371 national stage of international application PCT/FR01/03411 filed on Nov. 5, 2001, which designated the United States of America.

FIELD OF THE INVENTION

The present invention relates to a vertebral arthrodesis equipment.

BACKGROUND OF THE INVENTION

Equipment of such kind generally includes two shoring rods designed to be disposed parallel to one another on either side of the vertebrae to be treated, and assemblies for anchoring these rods to the vertebrae, in the form of hooks or pedicle screws. This equipment may also include crossmembers that approach these rods incrementally, for preserving their position relative to one another.

In order to attach a shoring rod to an anchoring assembly, the design has provided for the inclusion of two facing walls on the proximal portion of the anchoring assembly, these walls defining a seating for the rod therebetween and furnished with means, such as a threaded or tapping arrangement, for receiving a nut or threaded plug for locking the rod. These walls impart a "tuning fork" or "tulip" shape to this proximal portion, such names having now become the accepted designations for this type of assembly.

An existing hook on this type of equipment is designed to be engaged around the pedicle and for this purpose is furnished with a curved vane that is shaped correspondingly. However, the possibilities for implementing this hook are limited to one pedicle support point, which does not allow of adaptation for the various situations that may arise. In fact, in certain cases depending specifically on the position and orientation of the shoring rod with respect to this hook or depending on the quality of the vertebral bone, it may be preferable to select a different support area.

In extreme cases, the existing hook may also provoke doubts regarding the perfect resistance of the assembly that it allows.

The object of the present invention is primarily to remedy these essential disadvantages.

In addition, one significant disadvantage of the existing "tuning fork" ("tulip") hooks is that occasionally considerable effort is required to locate the rods inside the seating for these rods. When the pedicles are small in size, as is the case for thoracic vertebrae, particularly vertebrae D1 to D4, there is a danger that the pedicle may break and it is necessary to rely on hooks rather than screws. In view of the limitations described in the aforegoing, the existing hooks are not ideally suited for all situations that may arise.

A further disadvantage of the existing hooks is that their height is substantial due to the height of the said walls defining the seatings for a shoring rod. This height is not particularly inconvenient when the tissues are fairly thick, as is the case at the level of the lumbar vertebrae, but it does create difficulties when tissues become relatively thin, as is the case at the level of the thoracic vertebrae, when the equipment may be felt under the skin.

A further object of the present invention is to remedy this disadvantage.

SUMMARY OF THE INVENTION

The equipment to which the invention relates includes in known manner at least a shoring rod and at least an anchoring assembly of the shoring rod to a vertebra; each anchoring assembly comprises a base integral with a hook and means for attaching said shoring rod to the anchoring assembly; the hook has a curved base part, by means of which it is attached to the base, and a substantially planar part, extending in a parallel plane, or forming a slight angle, less than 15 degrees, with said base.

According to the invention, the base has a hole which runs right through it, extending in a parallel direction or forming a slight angle, as described in the aforegoing, with the longitudinal direction of said planar part of the hook; this hole opens towards the hook base in the form of an opening having a circular section and, apart from this opening, has an oblong cross-section, the length of which oblong cross-section extending on a parallel plane or forming a slight angle, as described in the aforegoing, with the plane in which said planar part extends; and the anchoring assembly comprises a hook-shaped component whereof the part corresponding to the base of the hook is linked to a threaded rod, said rod capable of being engaged in said hole with the possibility of pivoting about an axis and of displacement in said plane, and capable of receiving a nut at the end that protrudes through said opening, and which nut, when threaded enables the hook formed by the component to be drawn towards the hook that is integral with the base.

Each assembly thus includes a first hook, integral with said base, and a second hook, engaging with the first hook, which may be placed in various positions with respect to the first hook, specifically according to a number of pivoting positions about the axis of the threaded rod and according to a number of positions inclined with respect to the base, rendered possible by displacement of the rod in said hole.

It is possible to clamp two vertebral support zones between these two hooks, of which at least one zone may be chosen to correspond most closely to the anchorage to be effected in accordance with the position or orientation of the shoring rod and/or in accordance with the quality of the bone. The assembly according to the invention thus particularly enables pedicular-laminar, laminar-transverse process, pedicular-transverse process or laminar-laminar support areas.

The means for attaching a shoring rod to an anchorage assembly as described above advantageously include:

a boss integral with the base, defining an interior cavity that is at least partly spherical in shape, and defining on the outside a portion of a spherical wall; the centres that define the one or more spherical zones of the cavity and said portion of the spherical wall are offset with respect to each other in a direction perpendicular to the base;

a threaded rod including at one end thereof a convex base designed to be engaged and retained in said cavity on the base, the convex base being at least partly spherical in shape, so that it cooperates with the one or more spherical zones of the cavity so as to allow pivoting or articulation of the threaded rod relative to the base;

a stirrup piece having a rounded part suitable for receiving a shoring rod, two superposed wings perforated with holes to allow the stirrup piece to engage with said threaded rod, and a face in the shape of a portion of hollow sphere, which face being designed to abut said portion of the spherical wall when the stirrup piece is engaged in said threaded rod, and a nut that may be screwed onto the threaded rod so as to enable the stirrup piece to be tightened between the nut and said portion of the spherical wall.

Because of the cavity and the convex base, the threaded rod may be aligned towards the stirrup piece, which itself has already been engaged about the shoring rod. This alignment makes it easier for the eyelet on the stirrup piece to be engaged with this threaded rod.

The nut may then be engaged on the threaded rod and tightened, which has the effect of drawing said concave face of the stirrup piece into contact with said portion of the spherical wall of the boss and then, when such contact is made, and because of the offset between the two centres indicated previously, of drawing said threaded rod in a direction substantially perpendicular to the base as the nut is tightened further.

These means of assembly thus facilitate the implantation of the equipment and enable the shoring rod to be positioned progressively relative to the anchoring assemblies that constitute this equipment, which have been positioned on the vertebrae beforehand.

BRIEF DESCRIPTION OF THE DRAWINGS

For purposes of better understanding, the invention is described again in the following with reference to the attached schematic drawing, which represents a non-limiting, exemplary preferred embodiment of the equipment under consideration.

FIG. 1 is a perspective view, before assembly, of an anchoring assembly included therein;

FIGS. 2 to 4 are end, front and plan views respectively of a base and a hook included therein, and FIG. 5 is an enlarged partial view of a cross-section along line V—V in FIG. 1 after the anchorage assembly has been attached.

DETAILED DESCRIPTION OF THE INVENTION

FIG. 1 represents an anchorage assembly 1 forming part of a vertebral arthrodesis equipment.

This equipment includes two shoring rods, designed to be to be disposed parallel to one another and on either side of the vertebrae, and anchoring members for anchoring these rods to the vertebrae. These anchoring members may be pedicle screws and/or one or more anchoring assemblies 1. The equipment may further include cross-members that are designed to draw the shoring rods transversely together progressively, for preserving their position relative to one another.

These rods, pedicle screws and cross-members are known in and of themselves and are therefore not specifically described.

As is shown in FIG. 1, anchoring assembly 1 comprises a hook 2 integral with a parallelepiped base 3, a hook-shaped component 4 attached to a threaded rod 5, a screw 6 that may be screwed onto this threaded rod 5, a threaded rod 7, a stirrup piece 8, and a nut 9.

Hook 2 is furnished with a curved base part 2a, by means of which it is connected to base 3, and an substantially planar part 2b that forms an angle of eight degrees with face 3a of the base to which hook 2 is attached.

Base 3 is furnished with a hole 10 which passes completely therethrough. As is shown more specifically in FIGS. 3 and 4, this hole 10 is disposed overall in a direction parallel to face 3a of the base and in the longitudinal direction of planar part 2b. This hole 10 has openings in two lateral and opposite faces of base 3.; on the side facing base part 2a, this hole 10 has a circular opening 11 with a section slightly larger than the transverse section of rod 5; apart from this opening 11, hole 10 has an oblong cross-section, the length of which oblong cross-section extending parallel to face 3a.

Base 3 is also furnished with a boss 15 projecting from the main face 3b thereof which is opposite to face 3a. This boss 15 defines an interior cavity 16 and on the outside presents a face 17 in the form of a partly spherical wall.

FIGS. 3 and 4 show that cavity 16 is defined by two diametrically opposed zones 20 in the form of a hollow sphere and formed on the same radius and the same centre, and by two flattened surfaces 21, parallel to the lateral faces of base 3 in which hole 10 does not have an opening.

FIG. 5 shows that centres C1, C2 that create the one or more zones 20 and the portion of the sphere formed by face 17 are offset relative to each other along a direction perpendicular to said main faces 3a, 3b of base 3.

Component 4 includes a part 4a that is curved in the shape of a hook and a base part 4b. The base part 4b is attached to threaded rod 5.

This rod 5 has a diameter such that it may be engaged in hole 10 with the possibility of pivoting about its own axis and being displaced in this hole 10.

On the end that protrudes through hole 11, rod 5 may receive nut 6. As it is tightened, this nut thus enables hook 2 to be drawn towards the hook formed by part 4a of component 4.

Rod 7 is provided at one end thereof with a convex base 25 having two spherical zones and two flattened surfaces to yield a shape corresponding precisely with zones 20 and flattened surfaces 21. This base is engaged in cavity 16 when assembly 1 is created and then the lateral wall of boss 15 is fastened on this base 25 in such manner as to ensure that base 25 is retained in cavity 16, allowing rod 7 to be pivoted relative to base 3, by displacing the spherical zones towards each other.

Rod 7 is also furnished with a reduced section 30 that allows section thereof after the equipment has been finally assembled.

Stirrup piece 8 includes a rounded part 31 that defines a seating for the shoring rod, and two lateral wings 32, in which two holes 33 are superposed. These holes 33 enable stirrup piece 8 to be engaged with rod 7 so that the shoring rod is attached to assembly 1.

As is shown in FIG. 5, upper hole 33 is defined by a conical face 35, and lower hole 33 is defined partially by a face describing a hollow sphere having the same radius as face 17.

Assembly 1 thus includes a first hook 2 integral with base 3 and a second hook 4b, the counterpart of first hook 2, which may be placed in various positions relative to first hook 2, specifically according to a number of pivoting positions about the axis of threaded rod 5 and according to a number of positions inclined with respect to base 3, rendered possible by displacement of this rod 5 in hole 10. The assembly according to the invention thus particularly enables pedicular-laminar, laminar-transverse process, pedicular-transverse process or laminar-laminar support areas.

Moreover, because of cavity 16 and convex base 25, rod 7 may be aligned with the corresponding stirrup piece 8 at the time the equipment is placed in position, the stirrup piece itself having already been engaged about the shoring rod.

This alignment makes it easier for the holes 33 to be engaged with this rod 7. Nut 9 may then be engaged on rod 7 and tightened, which has the effect of drawing concave face 36 into contact with face 17 and then, when such contact is made, and because of the offset between the two centres C1, C2 indicated previously, of drawing rod 7 in a direction substantially perpendicular to base 3 as nut 9 is tightened further.

These means of assembly thus facilitate the implantation of the equipment and enable the shoring rod to be positioned progressively relative to the one or more anchoring assemblies 1 that constitute this equipment.

From the aforegoing, it may be seen that the invention provides a vertebral arthrodesis equipment having the significant advantages described previously with respect to related equipment and the prior art.

Of course, the invention is not limited to the embodiment described in the preceding text, which served an exemplary purpose only, but on the contrary may be extended to include all the variations covered in the attached claims.

The invention claimed is:

1. A vertebral arthrodesis equipment including at least a shoring rod and at least an anchoring assembly of the shoring rod to a vertebra; each anchoring assembly comprising a base integral with a first hook and means for attaching said shoring rod to the anchoring assembly; said first hook having a curved base part attached to the base, and a substantially planar part extending in a parallel plane, or forming a slight angle, less than 15 degrees, with said base; wherein:
   the base has a hole running therethrough, and extending in a parallel direction or forming a slight angle with the longitudinal direction of said planar part; said hole opening towards the base in the form of an opening having a circular section, and apart from said opening having an oblong cross-section; said oblong cross-section having a length which extends on a parallel plane or forms a slight angle with the plane in which said planar part extends; and
   the anchoring assembly comprises a second hook having a base part linked to a first threaded rod, said rod structured and arranged to engage in said hole with the possibility of pivoting about an axis and of displacement in said plane, and capable of receiving a nut at a rod end that protrudes through said opening; and said nut, when threaded, enabling the second hook to be drawn towards the first hook.

2. The equipment according to claim 1, wherein the means for attaching the shoring rod to the anchoring assembly include:
   a boss integral with the base, defining an interior cavity that is at least partly spherical in shape, and defining on the outside a portion of a spherical wall; the centers that define the one or more spherical zones of the cavity and the portion of the spherical wall being offset with respect to each other in a direction perpendicular to the base;
   a second threaded rod including at one end thereof a convex base designed to be engaged and retained in said cavity; said convex base being at least partly spherical in shape, so as to cooperate with the one or more spherical zones of the cavity and allow pivoting or articulation of the second threaded rod relative to the base;
   a stirrup piece having a rounded part suitable for receiving a shoring rod, two superposed wings perforated with holes to allow the stirrup piece to engage with said second threaded rod, and a face in the shape of a portion of hollow sphere; said face being designed to abut said portion of the spherical wall when the stirrup piece is engaged on said second threaded rod; and
   a nut that may be screwed onto the second threaded rod so as to enable the stirrup piece to be tightened between the nut and said portion of the spherical wall.

3. The equipment according to claim 2, wherein:
   the cavity is defined by two diametrically opposed zones in the form of a hollow sphere and formed on the same radius and the same center, and by two flattened surfaces, parallel to the lateral faces of the base in which the hole does not have an opening; and
   the convex base has two spherical zones and two flattened surfaces to yield a shape corresponding precisely with zones and flattened surfaces of the base.

4. The equipment according to claim 3, wherein the second threaded rod has a reduced section that allows section thereof after the equipment has been finally assembled.

5. The equipment according to claim 2, wherein the second threaded rod has a reduced section that allows section thereof after the equipment has been finally assembled.

* * * * *